United States Patent
Doyle

(10) Patent No.: US 7,617,824 B2
(45) Date of Patent: Nov. 17, 2009

(54) VENTILATOR ADAPTABLE FOR USE WITH EITHER A DUAL-LIMB CIRCUIT OR A SINGLE-LIMB CIRCUIT

(75) Inventor: Peter R. Doyle, Vista, CA (US)

(73) Assignee: RIC Investments, LLC, Wilmington, DE (US)

( * ) Notice: Subject to any disclaimer, the term of this patent is extended or adjusted under 35 U.S.C. 154(b) by 75 days.

(21) Appl. No.: 11/633,796

(22) Filed: Dec. 5, 2006

(65) Prior Publication Data
US 2007/0144516 A1    Jun. 28, 2007

Related U.S. Application Data
(60) Provisional application No. 60/748,503, filed on Dec. 8, 2005.

(51) Int. Cl.
*A61M 16/00* (2006.01)
(52) U.S. Cl. ............... 128/204.21; 128/204.23; 128/204.26; 128/204.18
(58) Field of Classification Search ........... 128/200.24, 128/200.26, 200.27, 203.12, 203.13, 203.22, 128/203.25, 203.26, 204.18, 204.21, 204.23, 128/205.11, 205.24, 207.12, 911
See application file for complete search history.

(56) References Cited

U.S. PATENT DOCUMENTS

| | | | |
|---|---|---|---|
| 4,232,667 A * | 11/1980 | Chalon et al. ........... 128/203.26 |
| 4,265,235 A * | 5/1981 | Fukunaga .............. 128/200.24 |
| 5,299,568 A * | 4/1994 | Forare et al. ........... 128/205.11 |
| 5,404,873 A * | 4/1995 | Leagre et al. .......... 128/204.18 |
| 5,490,499 A * | 2/1996 | Heinonen et al. ...... 128/203.28 |
| 5,664,562 A * | 9/1997 | Bourdon ............... 128/204.23 |
| 5,685,296 A | 11/1997 | Zdrojkowski et al. |
| 5,694,923 A | 12/1997 | Hete et al. |
| 5,701,883 A | 12/1997 | Hete et al. |
| 5,722,391 A * | 3/1998 | Rosenkoetter et al. . 128/200.24 |
| 5,894,839 A * | 4/1999 | Rosenkoetter et al. . 128/200.24 |
| 5,931,159 A * | 8/1999 | Suzuki et al. ......... 128/204.18 |
| 5,937,851 A | 8/1999 | Serowski et al. |
| 6,123,074 A | 9/2000 | Hete et al. |

(Continued)

OTHER PUBLICATIONS

Hamilton Medical, "Raphael Intelligent Ventilation", product brochure.

(Continued)

*Primary Examiner*—Justine R Yu
*Assistant Examiner*—Annette F Dixon

(57) ABSTRACT

A ventilator of the present invention includes a housing, a gas flow generator disposed in the housing, a gas outlet port provided on an exterior surface of the housing, and a first conduit coupling the gas flow generator to the gas outlet port. A gas inlet port is also provided on an exterior surface of the housing. A second conduit couples the gas inlet port to a first exhaust valve in the housing that regulates a flow of exhaust gas from the second conduit. A second exhaust valve in the housing is coupled to the first conduit and regulates a flow of exhaust gas from the first conduit. A controller coupled to second exhaust valve causes the second exhaust valve to change a degree of flow restriction based on a respiratory phase of a patient coupled to the ventilator when the ventilator is operating in a single-limb ventilation configuration.

13 Claims, 2 Drawing Sheets

U.S. PATENT DOCUMENTS

| | | |
|---|---|---|
| 6,584,977 B1 | 7/2003 | Serowski |
| 6,615,830 B1 | 9/2003 | Serowski et al. |
| 6,615,831 B1 | 9/2003 | Tuitt et al. |
| 6,851,425 B2 | 2/2005 | Jaffre et al. |
| 2004/0211422 A1 | 10/2004 | Arcilla et al. |

OTHER PUBLICATIONS

Hamilton Medical, "Raphael XTC Intelligent Ventilation", product brochure.

* cited by examiner

VENTILATOR ADAPTABLE FOR USE WITH EITHER A DUAL-LIMB CIRCUIT OR A SINGLE-LIMB CIRCUIT

CROSS-REFERENCE TO RELATED APPLICATIONS

This application claims priority under 35 U.S.C. § 119(e) from provisional U.S. patent application No. 60/748,503 filed Dec. 8, 2005 the entire contents of which are incorporated herein by reference.

BACKGROUND OF THE INVENTION

1. Field of the Invention

The present invention pertains to a system and method for ventilating a patient that allows a ventilator to be connected to the airway of a patient using either a single-limb breathing circuit or a dual-limb breathing circuit to optimize the flexibility of the ventilator and treatment options available for the patient.

2. Description of the Related Art

It is known to provide pressure support to a patient through a single-limb breathing circuit and a patient interface. Such ventilation systems typically generate a flow of gas using, for example, a blower. The pressure or flow of gas delivered to the patient is controlled by controlling the operating speed of the blower, controlling a valve that diverts gas from the gas flow path, or a combination thereof. The gas flow is communicated to the airway of the patient by means of the breathing circuit, which is usually a flexible tube coupled to a gas outlet port of the ventilator. The distal end of the single-limb breathing circuit includes the patient interface, such as a nasal mask, nasal/oral (full) mask, total face mask that covers the face, or nasal canula, that couples the breathing circuit to the airway of the patient.

An exhaust port is provided in the breathing circuit, the patient interface, at a coupling between the breathing circuit and the patient interface, or any combination thereof. The exhaust port allows gas to pass from the interior of the breathing circuit or patient interface to the ambient atmosphere. A typical exhaust port consists of a relatively small, fixed geometry orifice or a plurality of orifices. Variable geometry orifices are also known. During exhalation, some of the patient's expired gas passes to atmosphere via the exhaust port, and some expired gas flows back up the breathing circuit to toward the ventilator. It is possible, depending on the size of the expiration, for expired gas to exit the gas system through the pressure control valve in the ventilator.

This technique for exhausting gas through the exhaust port, and possibly through the pressure/flow control valve in the ventilator inspiratory limb, is advantageous in that there is a relatively low resistance to the expiratory flow. Thus, the expiratory effort (work) exerted by the patient during exhalation is minimized in ventilators that use a single-limb circuit to communicate the flow of gas to the patient. In addition to providing ventilation using a mask, single-limb ventilators, which are also referred to as pressure support systems, are used to provide various modes of pressure support, including, for example, continuous positive airway pressure (CPAP) support, bi-level pressure therapy that varies the treatment pressure with the user's respiratory cycle, proportional assist ventilation (PAV®) that varies the pressure with respiratory effort, proportional positive airway pressure (PPAP) ventilation that varies the pressure with flow or with a predetermined profile, auto-titration pressures support that varies the pressure based on a monitored condition of the user.

Critical care ventilators provide support to a patient using a dual-limb circuit that includes an inspiratory limb and an expiratory limb. Such ventilators are often referred to as "invasive" ventilators because the patient interface is typically a device inserted into the airway of the patient. However, it is known to use a non-invasive patient interface in a dual-limb ventilator. A flow of gas is typically generated by a compressor, blower, piston, or bellows. The inspiratory limb carries the flow of gas from the ventilator to the patient, and the expiratory limb carries the flow of gas from the patient to an exhaust valve, which is typically provided within the ventilator. The exhaust valve controls the flow of exhaust gas from the system, i.e., from the expiratory limb. The proximal portions of both the inspiratory limb and the expiratory limb are coupled to the ventilator, and the distal portions of both the inspiratory limb and the expiratory limb are connected to a Y-connector near the patient. The patient interface in a dual-limb ventilator, which is coupled to the Y-connector, is typically a tracheostomy tube or an endotracheal tube. However, it is known to use a nasal/oral mask to interface the breathing to the patient, so long as the leakage of gas from the mask is minimized.

It can be appreciated that one difference between a single-limb ventilator configuration and a dual-limb ventilator configuration resides in the ability of the ventilator to manage leaks. In a single-limb ventilator system, there is a known leak from the system through the exhaust port as well as potential unknown leaks, such as leaks at the mask/patient interface. Techniques are known and employed in a single-limb ventilator system to account for the known leak, as well as the unknown leaks, to ensure that the patient receives the desired pressure and/or flow. Thus, single-limb ventilator systems are also referred to as "leak tolerant" systems. In a dual-limb ventilator system, however, the system is closed, meaning that there are not supposed to be leaks, intentional or otherwise, so that the ventilator can precisely control the pressure, volume, and/or flow of gas delivered to and expired from the patient. Thus, dual-limb ventilator systems are not leak tolerant as they do not have the ability to account for leaks.

Because a dual-limb ventilator system has the ability to control the pressure, volume, and/or flow of gas delivered to the patient with greater accuracy than a single-limb ventilator system, dual-limb ventilator systems are better suited for use in life support situations. Conversely, dual-limb ventilator systems are not well suited to situations where non-invasive ventilation is desired, because of their inability to handle leaks, which are common when ventilating a patient non-invasively. In addition, when a conventional dual-limb ventilator system is used in a non-invasive ventilation mode, it is typically still used in a dual-limb configuration. However, this dual-limb configuration is disadvantageous because the presence of the expiratory limb results in a relatively high expiratory resistance (resistance to exhalation), which is typically higher than that present in conventional single-limb ventilator systems. This high expiratory resistance is due to the fact that the expiatory flow must pass through the entire expiratory limb, as well as through flow sensors, bacteria filters, and the exhaust valve.

It is also known to provide non-invasive ventilation in a critical care ventilator by providing a single-limb circuit having a proximal end coupled to the inspiratory limb portion of the ventilator and a distal end coupled to the patient interface. Conventional ventilators having this configuration use an actively controlled exhaust valve provided at the distal end of the single-limb circuit. In addition, a hardwired connection must be provided between the ventilator and the actively controlled valve, so that the ventilator can control the operation of the valve. More specifically, the valve is controlled to open (exhaust gas to atmosphere) during an expiratory phase of a breathing cycle and close during the inspiratory phase. This configuration is disadvantageous because it requires the relative bulky and cumbersome actively controlled valve to be "hung" from the distal end of the single-limb circuit, i.e., the location where the Y-connector would be in a dual-limb circuit. In addition, the hardwired connection to the actively controlled valve presents entanglement issues with the wire connection.

SUMMARY OF THE INVENTION

Accordingly, it is an object of the present invention to provide a ventilator that overcomes the shortcomings of conventional ventilators. This object is achieved according to one embodiment of the present invention by providing a ventilator that includes a housing, a gas flow generator disposed in the housing, a gas outlet port disposed on an exterior surface of the housing, a first conduit coupling the gas flow generator to the gas outlet port, a gas inlet port disposed on an exterior surface of the housing, a first exhaust valve disposed in the housing, and a second conduit coupling the gas inlet port to the first exhaust valve. The first exhaust valve controls a flow of exhaust gas from the second conduit. A second exhaust valve is disposed in the housing and is operatively coupled to the first conduit. The second exhaust valve controls a first flow of exhaust gas from the first conduit. In addition, a controller is operatively coupled to the second exhaust valve and causes the second exhaust valve to change a degree of flow restriction based on a respiratory phase of a patient coupled to the ventilator when the ventilator is operating in a single-limb ventilation configuration. Thus, the present invention provides the components of both dual-limb and a single-limb ventilator so that it can operate using either a dual-limb circuit or a conventional single-limb circuit without inducing a large expiratory resistance and without the need for a special single-limb circuit, such as that requiring an active exhaust valve near the patient.

In another embodiment of the present invention, this object is achieved by providing a system for providing ventilation to a patient that includes a ventilator, dual-limb circuit, and single-limb circuit. The ventilator includes a housing, a gas flow generator disposed in the housing, a gas outlet port disposed on an exterior surface of the housing and operatively coupled to the gas flow generator, a gas inlet port disposed on an exterior surface of the housing, a controller disposed in the housing and adapted to operate the ventilator in a single-limb ventilation configuration or a dual-limb ventilation configuration. The dual-limb circuit includes an inspiratory limb adapted to be coupled to the gas outlet port, and an expiratory limb adapted to be coupled to the gas inlet port when the ventilator is configured to operate in the dual-limb ventilation configuration. The single-limb circuit has a proximal end adapted to be coupled to the gas outlet port, when the ventilator is configured to operate in the single-limb ventilation configuration. The controller is adapted to operate the ventilator in the single-limb ventilation configuration when the single-limb circuit is coupled to the gas outlet port, or in the dual-limb ventilation configuration when the dual-limb circuit is coupled to the gas outlet port and the gas inlet port.

It is yet another object of the present invention to provide a method of providing ventilation to a patient that does not suffer from the disadvantages associated with conventional ventilation techniques. This object is achieved by providing a method that includes providing a ventilator that includes a housing, a gas flow generator disposed in the housing, a gas outlet port disposed on an exterior surface of the housing and operatively coupled to the gas flow generator, a gas inlet port disposed on an exterior surface of the housing, and a controller disposed in the housing and adapted to operate the ventilator in a single-limb ventilation configuration or an dual-limb ventilation configuration. The method further includes providing a dual-limb circuit comprising an inspiratory limb and an expiratory limb and providing a single-limb circuit having a proximal end coupled to the gas outlet port, when the ventilator is configured to operate in of the single-limb ventilation configuration. The method further involves selecting whether to operate the ventilator in a dual-limb ventilation configuration or the single-limb ventilation configuration, and coupling the dual-limb circuit to the ventilator when the dual-limb configuration is selected/desired, or coupling the single-limb circuit to the ventilator when the single-limb configuration is selected/desired.

In another embodiment of the present invention, this object is achieved by providing a ventilator that includes a housing, a gas flow generator disposed in the housing and adapted to generate a flow of gas, an exhaust valve disposed in the housing, a gas outlet port disposed on an exterior surface of the housing, a gas inlet port disposed on an exterior surface of the housing, a first conduit structured to couple the gas flow generator to the gas outlet port and to the exhaust valve, a second conduit structured to couple the gas inlet port to the exhaust valve, wherein the exhaust valve is structured to control a flow of exhaust gas from the first conduit and a flow of gas from the second conduit, and a controller operatively coupled to the exhaust valve, wherein the controller causes the exhaust valve to change a degree of flow restriction responsive to a respiratory phase of a patient coupled to the ventilator and responsive to the ventilator being configured to operate in a single-limb ventilation configuration or a dual-limb ventilation configuration.

In another embodiment of the present invention, this object is achieved by providing a system structured to provide ventilation to a patient. The system comprises a ventilator, a dual-limb circuit adapted to be coupled to the ventilator, responsive to the ventilator being configured to operate in the dual-limb ventilation configuration, and a single-limb circuit adapted to be coupled to the ventilator responsive to the ventilator being configured to operate in the single-limb ventilation configuration. The ventilator comprises a housing, a gas flow generator disposed in the housing and structured to generate the flow of gas, an exhaust valve, and a controller adapted to operate the ventilator in a single-limb ventilation configuration or a dual-limb ventilation configuration.

In another embodiment of the present invention, this object is achieved by providing a method for providing ventilation to a patient. The method comprises coupling such a patient to a ventilator with one of a single-limb circuit or a dual-limb circuit, and creating a flow of gas with the ventilator. The ventilator comprises a housing, a gas flow generator disposed in the housing and structured to generate the flow of gas, an exhaust valve, a gas outlet exhaust port disposed on an exterior surface of the housing and operatively coupled to the gas flow generator and to the exhaust valve, a gas inlet port disposed on the exterior surface of the housing and operatively coupled to the exhaust valve, and a controller operatively coupled to the exhaust valve, the controller adapted to cause the exhaust valve to change a degree of flow restriction responsive to a respiratory phase of such patient and responsive to such patient being coupled to the ventilator with the single-limb circuit or the dual-limb circuit.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
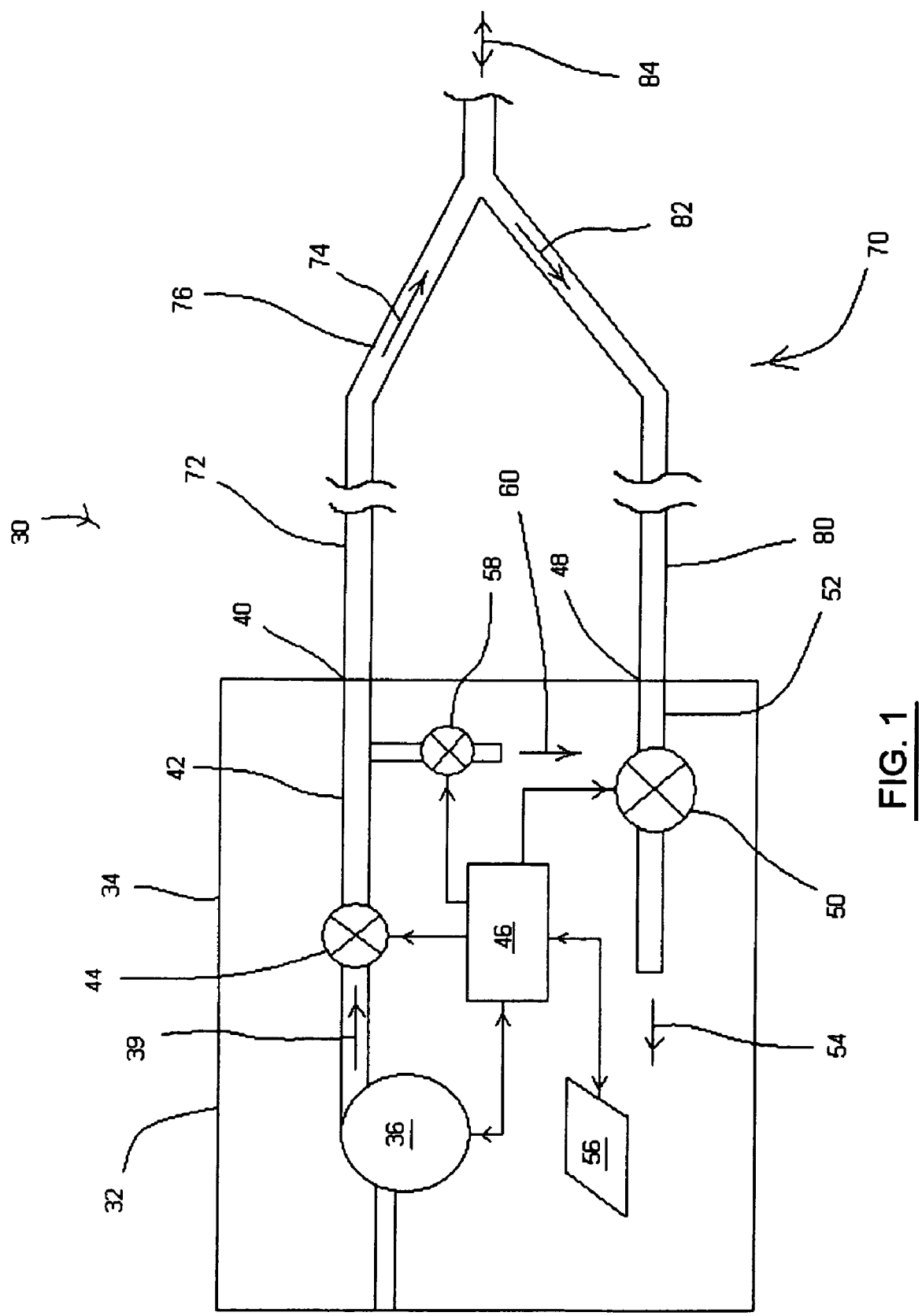
FIG. 1 is a schematic diagram of a ventilator according to the principles of the present invention shown coupled to a dual-limb patient circuit.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" together shall mean that the parts are joined together directly.

Figure 2:
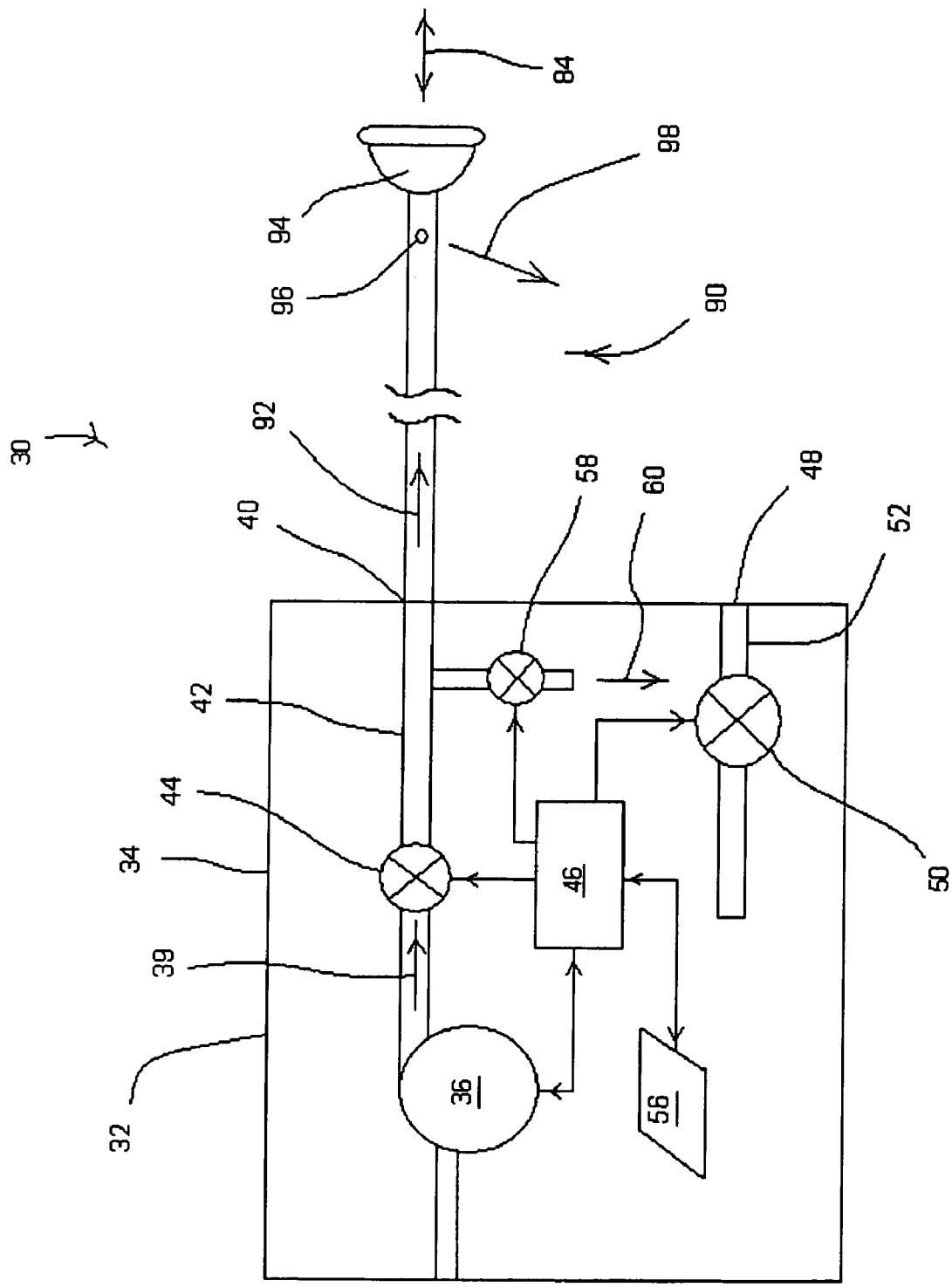
FIG. 2 is a schematic diagram of the ventilator of FIG. 1 shown coupled to a single-limb patient circuit.

FIGS. 1 and 2 schematically illustrate an exemplary embodiment of a ventilation system, generally indicated at 30, that includes a ventilator 32 according to the principles of the present invention. Ventilator 32 is capable of operating in either a dual-limb ventilation configuration, e.g., using a dual-limb circuit (FIG. 1), or a single-limb ventilation configuration using a conventional single-limb circuit, e.g., a single-limb conduit with a passive exhaust vent either associated with the conduit, a patient interface coupled to the conduit, or both (FIG. 2).

Ventilator 32 includes a housing 34 and a gas flow generator 36 disposed in the housing and adapted to generate a flow of gas. Gas flow generator 36 is any device suitable for creating a flow of gas, as indicated by arrow 39, at a pressure greater than ambient atmosphere, such as a compressor, fan, impeller, blower, piston, or bellows. Gas is provided to the gas flow generator from any suitable source, such as ambient atmosphere, a gas storage vessel (pressurized storage tank) or other gas supply.

Although not illustrated, the present invention further contemplates providing a secondary gas, such as oxygen, to the patient. Typically, the primary gas supply (air) is mixed with the secondary gas supply (e.g., oxygen) in the ventilator. The source of oxygen is typically a pressurized oxygen storage tank, a central wall supply (typically found in a hospital), or an oxygen concentrator. The secondary gas is often provided by a pressurized source, or a pressure generator that is provided in the ventilator or external thereto, to elevate the pressure of the secondary gas supply. Mixing of the primary gas flow and the secondary gas can be done upstream or downstream of gas flow generator 36. In addition, the present invention contemplates controlling the flow of the secondary gas and/or the mixing of the secondary gas with the primary gas flow so that the desired concentration of the secondary gas, e.g., $FIO_2$, is delivered to the patient. Techniques for monitoring the gas concentration and controlling the secondary gas in feedback fashion are well known. Therefore, they are omitted from the present application.

A gas outlet port 40 is disposed on an exterior surface of the ventilator housing. A first conduit 42 couples the output of the gas flow generator to the gas outlet port, so that a flow of gas is provided from the ventilator. In this illustrated embodiment, a valve 44 is coupled to conduit 42 to control the pressure/flow of gas provided by gas flow generator 36 to the patient. The present invention contemplates that valve 44 is any conventional pressure/flow control valve suitable for providing the pressure/flow control function. An example of a suitable valve is disclosed in U.S. Pat. Nos. 5,694,923; 5,701,883; 6,123,074; 6,615,831; and U.S. patent application Ser. No. 10/832,184 (Publication No. US 2004-0211422 A1). A controller 46 is coupled to valve 44 and/or gas flow generator 36 to control the pressure/flow of gas delivered to the patient.

The present invention also contemplates that the pressure/flow control functions of the ventilator can be accomplished by the gas flow generator alone, i.e., without valve 44. Thus, valve 44, in one embodiment, is optional. For example, the present invention contemplates controlling the pressure/flow by varying the operating speed of the gas flow generator, as is known in the art.

Conversely, in another embodiment, the present invention contemplates eliminating the gas flow generator and using the valve to control the pressure/flow of gas delivered to the patient. This is possible so long as the gas from the gas source, such as a pressurized storage vessel or pressurized gas source, is already pressurized. In this embodiment, in which gas flow generator 36 is optional, valve 44 operates as a pressure control valve to control the pressure/flow of gas delivered to the patient. Of course, the present invention also contemplates using a combination of both pressure/flow techniques, i.e., controlling the operating speed of the gas flow generator and providing a pressure/flow control valve or valves.

A gas inlet port 48 is disposed on an exterior surface of the housing, and a first exhaust valve 50 disposed in the housing is coupled to the gas inlet port via a second conduit 52. First exhaust valve 50 controls a flow of exhaust gas, as indicated by arrow 54, from the second conduit 52 and operates under the control of controller 46. First exhaust valve 50 corresponds to the exhaust valve in a typical critical care, dual-limb ventilator. For example, first exhaust valve 50 operates under the control of controller 46 to control the patient's expiration and positive end expiratory pressure (PEEP).

Ventilator includes an input/output device 56 in communication with controller 46. Input/output device 56 is any device, suitable for providing information to or receiving information from the controller, which is typically used to set up and/or control the ventilator. Examples of such devices include a keypad, touchscreen, display, buttons, switches, knobs, dials, LEDs, speakers, microphones, or any combination thereof provided directly on the ventilator. The present invention further contemplates that the input/output device can be remote or external to the housing of the ventilator, with a hardwired or wireless communication link being used to communicate the remote device with the controller to set up and/or control the ventilator. In which case, an appropriate terminal, receiver, transmitter, or transceiver is provided in the ventilator. Moreover, the remote communication with the ventilator can take place over a computer networks, such as the internet or an LAN system, which the appropriate communication link, such as modem, cable connection, RS-232, T1, DSL, being provided on the ventilator.

In the illustrated exemplary embodiment, ventilator 32 includes a second, actively controlled, exhaust valve 58 disposed within the ventilator housing and operatively coupled to first conduit 42. Second exhaust valve 58 controls a first flow of exhaust gas, as indicated by arrow 60, from the first conduit under the control of controller 46. In this illustrated embodiment, the flow of exhaust gas is vented to the ambient atmosphere. However, the present invention also contemplates directing all or a portion of the exhaust flow back to the inlet of gas flow generator 36. By providing second exhaust valve 58 in the pneumatic circuit associated with the gas flow generator, and by operating this exhaust valve in the same manner as done in a conventional non-invasive ventilator, i.e., a single-limb pressure support system, ventilator 32 of the present invention is capable of operating in a dual-limb, critical care, (typically invasive) mode of ventilation and is also capable of operating in a single-limb, pressure support, non-invasive mode of ventilation.

FIG. 1 illustrates ventilator 32 coupled to a dual-limb patient circuit 70. In this configuration, an inspiratory limb 72 carries a flow of gas from the ventilator to a patient, as indicated by arrow 74. A proximal end of the inspiratory limb is coupled to gas outlet port 40, and a distal end of inspiratory limb 72 is coupled to a Y-connector 76. An expiratory limb 80 carries a flow of gas from the patient, as indicated by arrow 82, back to ventilator 32, and, in particular, to first exhaust valve 50. A proximal end of the expiratory limb is coupled to gas inlet port 48, and a distal end is coupled to Y-connector 76.

During operation, a flow of gas, which is air, an air-oxygen, mixture, or any other conventional gas mixture, is generated by gas flow generator 36. Valve 44 controls the pressure/flow of gas output by the ventilator at outlet port 40. Inspiratory limb 72, which is typically a flexible hose or conduit, carries the flow of gas to the airway of the patient, i.e., via the Y-connector. The Y-connector is coupled to the airway of the patient using any conventional patient interface device suitable for use in this environment, such as a tracheal tube, endotracheal tube, or a mask. Patient respiration, whether spontaneous or driven by the ventilator, is illustrated by arrow 84.

During inspiration, valves 50 and 58 are closed, or at least restricted sufficiently, so that a flow of gas is delivered to the lungs of the patient and little or no gas is exhausted from these valves. During expiration, valve 58 remains closed, but valve 50 is actuated, so that gas can flow from the patient, down the expiratory limb, which is also typically a flexible hose or conduit, and exhausts from the expiratory limb. As noted above, the degree of opening of valve 50 can be controlled to control the pressure, e.g., PEEP, in the entire pneumatic system.

As noted above, valve 58 remains closed while the ventilator is operating in a dual-limb configuration. However, the present invention also contemplates using valve 58 as a pressure relief valve while the ventilator is operating in the dual-limb configuration. Namely, the present invention contemplates monitoring the pressure in conduit 42, inspiratory limb 72, or both and actuating valve 58 only if the monitored pressure exceeds a given threshold, which is typically a safety threshold. Of course, a conventional pressure relief valve, such as a pop-off valve, can be used alone or in combination with valve 58 to provide this safety feature. It can thus be appreciated that when operating in the dual-limb configuration, ventilator 32 operates in much the same manner as a conventional critical care ventilator.

Ventilator 32 is also capable of operating in a single-limb configuration using a conventional single-limb circuit, i.e., a circuit without a special active exhaust valve disposed near the patient. FIG. 2 illustrates ventilator 32 coupled to a single-limb circuit 90 according to one embodiment. Single-limb circuit 90 includes a single-lumen conduit 92, which is typically a flexible hose, having a proximal end coupled to outlet port 40 of ventilator 32, and a patient interface 94 coupled to a distal end of conduit 92. Patient interface 94 couples the conduit to an airway of the patient. In the illustrated embodiment the patient interface assembly 94 is a mask that covers the nose, mouth, of both. The present invention also contemplates that other devices for communicating a flow of gas to an airway of a patient, such as a mouthpiece, or combination nasal/oral masks, full face mask, tracheal tube, or endotracheal tube are suitable for use as patient interface device 94. In addition, headgear, a mouthpiece, or other device for securing the patient interface device to the user are not shown in the figures, but are contemplated for use in the present invention.

In the illustrated embodiment, single-limb circuit 90, i.e., conduit 92 and/or patient interface 94, includes a suitable exhaust assembly 96 for exhausting gas from these components to ambient atmosphere. In this embodiment, exhaust assembly 96 is defined by a passive exhaust port, i.e., a continuously open port, defined in conduit 92. The flow of gas provided by the exhaust port is indicated by arrow 98. Examples of suitable passive exhaust ports are taught, for example, in U.S. Pat. Nos. 5,937,851; 6,615,830; and 6,851, 425 and, the contents of which are hereby incorporated by reference.

It is to be understood that the present invention contemplates using other conventional passive exhaust assemblies as exhaust assembly 96. For example, U.S. Pat. Nos. 5,685,296 and 6,584,977 teach a plateau exhalation valve that provides a constant exhaust flow despite pressure fluctuations in the pneumatic system, suitable for use herein. For present purposes, a passive exhaust assembly is an assembly that is not electronically controlled, for example, by a separate controller.

During operation in the single-limb mode, controller 46 causes second exhaust valve 58 to change a degree of flow restriction, for example to open and close, based on a respiratory phase of a patient coupled to the ventilator. More specifically, during inspiration, valve 58 is closed so that exhaust flow 60 is blocked, and a flow of gas is provided to the patient. During expiration, however, valve 58 is opened, fully or partially, permitting exhaust gas flow 60, and the patient exhales into patient interface 94 and conduit 92. The exhaled gas is exhausted to atmosphere via exhaust assembly 96. Depending on the size of the exhalation, gas may also flow retrograde back up conduit 92 to exhaust valve 58. Because this valve is open during expiration, the expiratory flow is permitted to pass relatively unimpeded from the pneumatic system. Due to the presence of exhaust assembly 94 and the exhaust valve 58, there is very little resistance to expiratory flow. Thus, ventilator 32 functions well, for example in delivering non-invasive ventilation, using any conventional single-limb patient circuit.

The present invention also contemplates that the operating speed of gas flow generator 36 can by used in the single-limb configuration to vary the pressure/flow of gas to the patient, either alone or in combination with exhaust valve 58. That is, the present invention contemplates eliminating exhaust valve 58 in favor of using the operating speed control as the technique for increasing and decreasing the pressure of the flow of gas provided to the patient through the single-limb circuit. In addition, valve 44 can be used alone or in combination with gas flow generator 36 and/or exhaust valve 58, to provide the pressure/flow changing functions between inspiration and expiration when using a single-limb circuit connected to the outlet port of the ventilator.

It can be appreciated from the foregoing description of the present invention that ventilator 32 can be operated in a single-limb or a dual-limb configuration. The input/out device can be use to select which mode of operation the ventilator is to assume. The present invention also contemplates providing the ability to detect whether the ventilation system is set up in the dual-limb or the single-limb configuration automatically, i.e., without user input. For example, if there is no conduit coupled to inlet port 48, the ventilator can be programmed to default to the single-limb operating configuration. Switching between the single-limb ventilation configuration and the dual-limb configuration merely involves uncoupling the dual-limb circuit from the ventilator, and coupling single-limb circuit to the ventilator (or vice versa) and either switching the operating mode using the input/output device, or having the ventilator automatically determine which mode to operate in based on what circuits are connected to its ports.

The present invention contemplates that the conduits and/or valving in ventilator 32 can be discrete components or can be integrated in to a single unit, such as a single block of material. For example, exhaust valve 50 and exhaust valve 58 can be combined into a single, three-way exhaust valve. In this embodiment, first conduit 42 couples gas outlet port 40 to both gas flow generator 36 and this combined exhaust valve. Additionally, second conduit 52 couples gas inlet port 48 to this combined exhaust valve. The present invention further contemplates that features and components typically used in invasive or non-invasive ventilators can be employed in the ventilator of the present invention. For example, a humidifier, flow sensors, pressure sensors, temperature sensors, humidity sensors, bacteria filters, circuit heaters, etc., can all be used in the ventilation system of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. The features of exhaust valve 50 and exhaust valve 58, for instance, can be combined into a single, three-way exhaust valve while remaining within the scope of the present invention. Where exhaust valve 50 and exhaust valve 58 are combined in a single, three-way exhaust valve, it is contemplated that controller 46 may be structured to cause ventilator 32 to operate in a single-limb configuration even where a dual-limb conduit 72 is coupled to ventilator 32 (assuming that the necessary exhaust port is added to the dual limb conduit).

What is claimed is:

1. A ventilator comprising:
   a housing;
   a gas flow generator disposed in the housing and adapted to generate a flow of gas;
   a gas outlet port disposed on an exterior surface of the housing;
   a first conduit coupling the gas flow generator to the gas outlet port;
   a gas inlet port disposed on an exterior surface of the housing;
   a first exhaust valve disposed in the housing; a second conduit coupling the gas inlet port to the first exhaust valve, wherein the first exhaust valve controls a flow of exhaust gas from the second conduit;
   a second exhaust valve disposed in the housing and operatively coupled to the first conduit, wherein the second exhaust valve controls a first flow of exhaust gas from the first conduit; and
   a controller operatively coupled to the second exhaust valve, wherein the controller causes the second exhaust valve to change a degree of flow restriction based on a respiratory phase of a patient coupled to the ventilator responsive to the ventilator being configured to operate in a single-limb ventilation configuration.

2. The ventilator of claim 1, wherein the second exhaust valve is configured and arranged to exhaust the flow of gas from the first conduit to ambient atmosphere, to an inlet of the gas flow generator, or both.

3. The ventilator of claim 1, further comprising a pressure sensor adapted to monitor a pressure of gas in the first conduit, wherein the controller causes the second exhaust valve to change a degree of flow restriction responsive based on an output of the pressure sensor.

4. The ventilator of claim 1, wherein the ventilator is adapted to operate in a dual-limb ventilation configuration or in the single-limb ventilation configuration, wherein the controller causes the first exhaust valve to change a degree of flow restriction based on a respiratory phase of such a patient responsive to the ventilator operating in the dual-limb ventilation configuration.

5. The ventilator of claim 1, further comprising
   a dual-limb circuit comprising an inspiratory limb adapted to be coupled to the gas outlet port, and an expiratory limb adapted to be coupled to the gas inlet port, responsive to the ventilator being configured to operate in a dual-limb ventilation configuration; or
   a single-limb circuit having a proximal end adapted to be coupled to the gas outlet port, responsive to the ventilator being configured to operate in the single-limb ventilation configuration.

6. The ventilator of claim 5, further comprising:
   a patient interface coupled to a distal end of the single-limb circuit; and
   a passive exhaust assembly disposed in the patient interface, the single-limb circuit, or both to provide a second flow of exhaust gas to ambient atmosphere.

7. The ventilator of claim 1, further comprising an input device adapted to receive user-input selecting a dual-limb ventilation configuration or the single-limb ventilation configuration.

8. A ventilator comprising:
   a housing; a gas flow generator disposed in the housing and adapted to generate a flow of gas;
   an exhaust valve disposed in the housing;
   a gas outlet port disposed on an exterior surface of the housing;
   a gas inlet port disposed on an exterior surface of the housing;
   a first conduit structured to couple the gas flow generator to the gas outlet port and to the exhaust valve;
   a second conduit structured to couple the gas inlet port to the exhaust valve, wherein the exhaust valve is structured to control at least one of a flow of exhaust gas from the first conduit and a flow of gas from the second conduit; and a controller operatively coupled to the exhaust valve, wherein the controller causes the exhaust valve to change a degree of flow restriction responsive to a respiratory phase of a patient coupled to the ventilator and responsive to the ventilator being configured to operate in a single-limb ventilation configuration or a dual-limb ventilation configuration.

9. The ventilator of claim 8, further comprising a pressure sensor adapted to monitor a pressure of gas in the first conduit, wherein the controller causes the exhaust valve change a degree of flow restriction responsive based on an output of the pressure sensor.

10. The ventilator of claim 8, further comprising
a dual-limb circuit comprising an inspiratory limb adapted to be coupled to the gas outlet port, and an expiratory limb adapted to be coupled to the gas inlet port, responsive to the ventilator being configured to operate in a dual-limb ventilation configuration; or
a single-limb circuit having a proximal end adapted to be coupled to the gas outlet port, responsive to the ventilator being configured to operate in the single-limb ventilation configuration.

11. The ventilator of claim 10, further comprising:
a patient interface coupled to a distal end of the single-limb circuit; and
a passive exhaust assembly disposed in the patient interface, the single-limb circuit, or both to provide a flow of exhaust gas to ambient atmosphere.

12. The ventilator of claim 8, further comprising an input device adapted to receive user-input selecting the dual-limb ventilation configuration or the single-limb ventilation configuration.

13. A method for providing ventilation to a patient, comprising:
(a) coupling such a patient to a ventilator with one of a single-limb circuit or a dual-limb circuit; and
(b) creating a flow of gas with the ventilator, the ventilator comprising:
(1) a housing,
(2) a gas flow generator disposed in the housing and structured to generate the flow of gas,
(3) an exhaust valve,
(4) a gas outlet exhaust port disposed on an exterior surface of the housing and operatively coupled to the gas flow generator and to the exhaust valve,
(5) a gas inlet port disposed on the exterior surface of the housing and operatively coupled to the exhaust valve; and
(6) a controller operatively coupled to the exhaust valve, the controller adapted to cause the exhaust valve to change a degree of flow restriction responsive to a respiratory phase of such patient and responsive to such patient being coupled to the ventilator with the single-limb circuit or the dual-limb circuit.

* * * * *